United States Patent [19]

Arguelles

[11] Patent Number: 5,808,084

[45] Date of Patent: Sep. 15, 1998

[54] PROCESS FOR THE PREPARATION OF 1,4-DIHYDROPYRIDINEDICARBOXYLIC ESTERS

[75] Inventor: Rafael Arguelles, West Harrison, N.Y.

[73] Assignee: Pfizer, Inc., New York, N.Y.

[21] Appl. No.: 801,083

[22] Filed: Feb. 14, 1997

[51] Int. Cl.$^6$ .................................................. C07D 211/02
[52] U.S. Cl. ............................................................. 546/249
[58] Field of Search ............................................... 546/249

[56] References Cited

U.S. PATENT DOCUMENTS 4,600,778   7/1986   Teller et al. .............................. 546/249

*Primary Examiner*—Patrica L. Morris
*Attorney, Agent, or Firm*—Peter C. Richardson; Gregg C. Benson; Robert F. Sheyka

[57] ABSTRACT

Benzylidene intermediates, useful in the preparation of dihydropyridines such as nifedipine and amlodipine, are formed by reaction of a ketocarboxylic acid ester with an aldehyde in the presence of a catalytic amount of dimethylamine acetate.

11 Claims, No Drawings

PROCESS FOR THE PREPARATION OF 1,4-DIHYDROPYRIDINEDICARBOXYLIC ESTERS

This application is based on provisional application no. 60/011,660, filed on Feb. 14, 1996, the priority of which is hereby claimed.

BACKGROUND OF THE INVENTION

The present invention relates to a process for the preparation of known 1,4-dihydropyridinedicaboxylic esters.

Several processes for their preparation have already been disclosed.

Kirchner, Ber, 25,2786 (1892) refers to the reaction of aldehydes with 3-ketocarboxylic esters and ammonia in accordance with the reaction diagram below:

RCHO + 2R$_1$—CO—COOR$_2$ + NH$_3$ ⟶

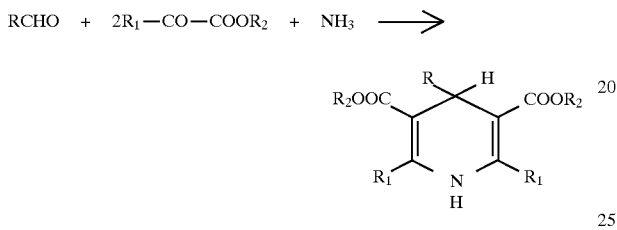

Fox et al. J. Org. Chem. 16, 1259 (1951) refers to the reaction of aldehydes with 3-ketocarboxylic esters and enaminocarboxylic esters in accordance with the reaction diagram below:

RCHO + R$_1$—CO—CH$_2$—COOR$_2$ + ⟶

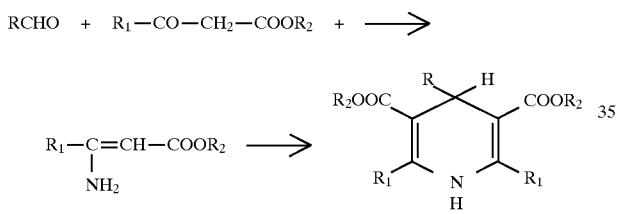

Knoevenagel, Ber. 31,743 (1898) describes the reaction of ylidene-3-ketocarboxylic esters with enaminorboxylic esters In accordance with the reaction diagram below:

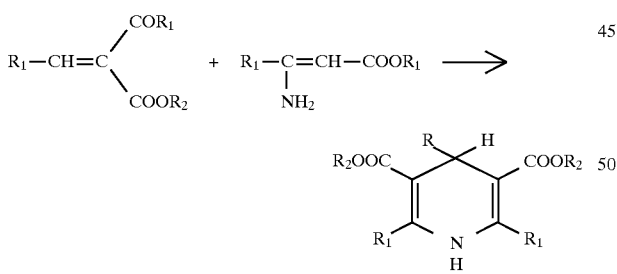

Since both aldehydes and ammonia react with ketocarboxylic esters, the ylidene compound and the enamine compound are also initially formed in the two above-mentioned processes.

DE-AS (German Published Specification) No. 2,117,573 describes the one-step preparation of unsymmetrical dihydropyridines by reaction of aldehydes with ketocarboxylic acids and enaminocarboxylic esters. A two-step process is regarded as having disadvantages, since the ylidene-β-ketocarboxylic esters, which can be prepared from aldehydes and ketocarboxylic esters, are very difficult to Isolate in the pure form and frequently only in low yields.

U.S. Pat. No. 4,600,778 refers to a process to produce dihydropyridines by reacting a ketocarboxylic ester with an aldehyde in the presence of piperidine acetate, and other amino acetate catalysts.

Since 1,4-dihydropyridines are useful as medicaments, there is a continuous need to make these compounds available in a high degree of purity. Thus, for example, preparation of 4-(2'-nitrophenyl)-2,6-dimethyl-3,5-dicarboethoxy-1,4-dihydropyridine by the method of U.S. Pat. No. 3,485,847, showed seven by products which could be detected by thin-layer chromatography.

SUMMARY OF THE INVENTION

The present Invention relates to a process for the preparation of 1,4-dihydropyridines of the formula I

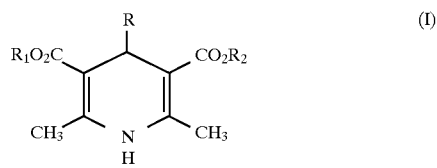

in which
  R represents a phenyl radical which Is optionally substituted once or twice by nitro and/or chlorine,
  R$_1$ represents a C$_1$–C$_4$ alkyl radical which Is optionally substituted by a C$_1$–C$_4$ alkoxy group, and
  R$_2$ represents a C$_1$–C$_{12}$ alkyl radial which is optionally substituted by a C$_1$–C$_4$ alkoxy group optionally substituted by an amino group, a trifluoromethyl group or the radical [C$_6$H$_5$CH$_2$][CH$_3$]N—, by reaction of an ylidene compound of the formulae II or III

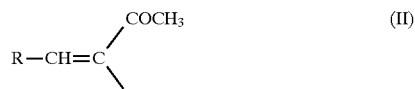

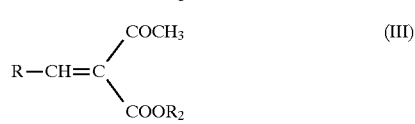

with an enamine compound of the formulae IV or V

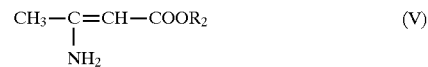

characterized In that the ylidene compounds of the formulae II or III are prepared by reaction of a ketocarboxylic ester of the formula VI or VII

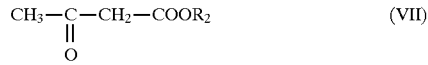

with an aldehyde of the formula RCHO or an acetal of said aldehyde, in a solvent, in the presence of catalytic amounts of dimethylamine acetate, at temperatures from −10° C. to 100° C.

The solvents which are preferably used are aliphatic alcohols, such as methanol, ethanol and/or isopropanol. The preferred reaction temperatures are 20°–60° C.

The catalyst is preferably added In amounts from 0.01 to 0.7 mole, particularly preferably from 0.02 to 0.2 mole, especially from 0.04 to 0.2 mole, per mole of aldehyde compounds.

It is possible and preferred to use 1 to 2 moles, especially 1 mole, of aldehyde per mole of ketocarboxyic ester of the formula VI or VII.

DETAILED DESCRIPTION OF THE INVENTION

In the formula I,

R preferably denotes a 2- or 3-nitrophenyl radical, a 2- or 3-chlorophenyl radical or a 2,3-dichlorophenyl radical $R_1$ preferably denotes methyl, ethyl, propyl, isopropyl, isobutyl or a propoxyethyl radical, and $R_2$ preferably denotes methyl, ethyl, propyl, isopropyl, isobutyl, n-decyl, methoxyethyl, propoxyethyl, trifluoromethyl, methoxyethylamino $[C_6—H_5CH_2][CH_3]N—$ or the radical $[C_6H_5CH_2][CH_3]N$.

The reaction of the ylidene compound of the formulae II or III with the enamine compound of the formulae IV or V is carried out at temperatures from −10° to 130° C., preferable from about 50° to 100° C.

It is possible and preferred to employ 1 to 1.5 moles, particularly preferably 1 to 1.3 especially 1 to 1.2 moles, of the enamine compound per mole of ylidene compound.

According to a particular embodiment, the crystalline ylidene compound remains in the reaction vessel and is directly reacted with the enamine compound.

It is also extremely surprising that, in the reaction according to the invention in the presence of the catalysts mentioned, the ylidene-3-ketocarboxylic esters are produced in high purity and excellent yield and can, if desired, be very readily isolated.

Furthermore, it has to be denoted surprising that the 1,4-dihydropyridine compounds are produced in such high purity and can be isolated in the manner described. Omitting a further purification process, they contain no by-products.

The process according to the invention has a number of advantages.

Thus, the yield is higher than according to the known processes, and the isolated product need not undergo any further purification steps.

When o-nitrobenzaldehyde, methyl acetoacetate and methyl 3-aminocrotonate are used as the starting materials, the course of the reaction can be represented by the diagram below:

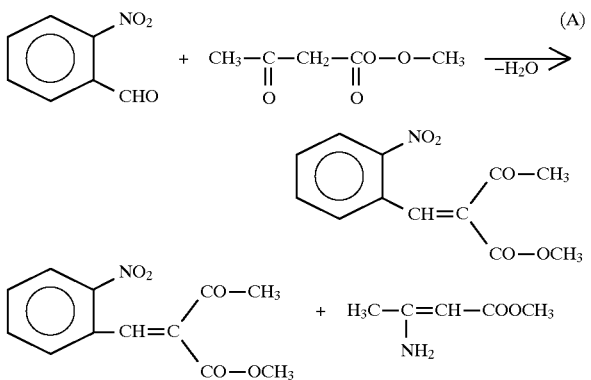

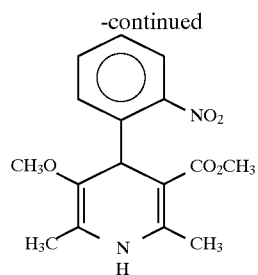

Having described the invention in general terms, reference is now made to specific examples. It is to be understood that these examples do not limit the present invention, the scope of which is determined by the appended claims.

EXAMPLE 1

Preparation of methyl 2-(2'nitrobenzylidene) acetoacetate

A mixture of 217 g of isopropanol, 40.0 g of o-nitrobenzaldehyde, 32.0 g of methylacetoacetate, 0.61 g of acetic acid and 4.78 g of 9.2% w/w methanolic dimethylamine was heated to between 39° and 41° C. for 15 minutes then cooled to 22° C. The product usually precipitates during the cooling period, but i necessary the o-nitrobenzylidene crystals may be added as seed. The slurry was granulated for 16 hours at a temperature between 18° and 22° C. The slurry was later cooled to between 0° and 5° C. and granulated for one hour. The product was isolated and washed with cold isopropanol, and dried overnight in a vacuum oven at 40° C. Isolated yield: 97.1%, melting range: 99° to 100° C.

EXAMPLE 2

Preparation of methyl 2-(2'-anisalidene) acetoacetate

A mixture of 16.45 g of isopropanol, 7.022 g of O-anisaldehyde, 6.236 g of methylacetoacetate, 0.167 g of acetic acid and 1.0132 g of 9.2% w/w methanolic dimethylamine was heated to between 39° and 41° C. for 15 minutes then cooled to 22° C. The product did not precipitate during the cooling period. The mixture was stirred for 16 hours at a temperature between 18° and 22° C. The product precipitated when the reaction mixture was transferred to another flask. The product was isolated, washed with cold isopropanol, and dried overnight in a vacuum oven at 40° C. Isolated yield 78.0%, melting range: 104° to 106° C.

EXAMPLE 3

Preparation of methyl 2-(4'-nitrobenzylidene) acetoacetate

A mixture of 7.37 g of isopropanol, 3.4772 g of p-nitrobenzaldehyde, 2.8247 g of methylacetoacetate, 0.0695 g of acetic acid and 0.4722 g of 9.2% w/w methanolic dimethylamine was heated to between 39° and 41° C. for 15 minutes then cooled to 22° C. The product usually precipitated during the cooling period, but if necessary the o-nitrobenzylidene crystals may be added as seed. The slurry was granulated for 16 hours at a temperature between 18° and 22° C. The slurry was later cooled to between 0° and 5° C. and granulated for one hour. The product was Isolated, washed with cold isopropanol and dried overnight in a vacuum oven at 40° C. Isolated yield: 88.6% melting range: 128° to 130° C.

EXAMPLE 4

Preparation of methyl 2-(3'-anisalidene) acetoacetate

A mixture of 18.74 g of isopropanol, 8.0149 g of o-anisaldehyde 7.1283 g of methylacetoacetate, 0.1472 g of acetic acid and 1.1572 g of 9.2% w/w methanolic dimethylamine was heated to between 39° and 41° C. for 15 minutes, then cooled to 22° C. The product usually precipitates during the cooling period, but if necessary the m-anisalidene crystals may be added as seed. The slurry was granulated for 16 hours at a temperature between 18° and 22° C. The slurry was later cooled to between 0° and 5° C. and granulated for one hour. The product was isolated, washed with cold isopropanol, and dried overnight in a vacuum oven at 40° C. Isolated yield: 58.3%, melting range: 64° to 65° C.

EXAMPLE 5

Preparation of methyl 2-(2'chlorobenzylidene) acetoacetate

A mixture of 60.10 g of isopropanol, 9.3 g of o-chlorobenzaldehyde, 7.98 g of methylacetoacetate, 0.16 g of acetic acid and 1.3 g of 9.2% w/w methanolic dimethylamine was heated to between 39° and 41° C. for 15 minutes then cooled to 22° C. The product did not precipitate. The mixture was stirred for 16 hours at a temperature between 18° and 22° C., concentrated and 200 ml of ethyl acetate was added. The ethyl acetate solution was extracted twice with water to remove the amine salt, concentrated and the resulting oil was purified by flash chromatography (silica gel column, hexane/ethyl acetate, 4:1). Isolated yield, mixture of isomers (corrected for o-chlorobenzaldehyde by $^1$H NMR): 85.8%.

EXAMPLE 6

Preparation of o-nitrobenzylidene, starting from o-nitrobenzaldehyde dimethylacetal To a round bottom flask was added 158 ml of water, and 3.4 g of concentrated sulfuric acid. The mixture was heated to 60° C., and over a period of 15 min. was added 157.8 g of o-nitrobenzaldehyde dimethylacetal. The mixture was distilled at 250 mbar until no more methanol/water condensed, not letting the pot's temperature exceed 65° C. at any time. A sample of the reaction mixture was taken to determine reaction completion (>97% o-nb). Distillation was at 60° to 65° C. until a sample met the IPC. The reaction mixture was transferred to a funnel with a jacket. Water at 60° to 65° C. was circulated through the jacket to keep the reaction mixture warm and the organic and aqueous phases were allowed to separate.

To another round bottom flask was added 510.8 g of isopropanol. The organic layer in the funnel was transferred to this flask. To this mixture was added 96.8 g of methylacetoacetate, 2.0 g of acetic acid and a calculated volume of methanolic dimethylamine (using the formula below). The mixture was heated to between 39° and 41° C. and kept at this range for 15 minutes. The reaction mixture was then cooled to between 18° and 22° C. Benzylidine crystals were added as seed, if necessary, and granulated for 16 hours. The slurry was cooled to between 0° and 5° C. and granulated for one hour, filtered, washed with cold Isopropanol and dried overnight in a vacuum oven at 40° C.

moles of dimethylamine×45.09 a (molecular wt. DMA). grams of solution concentration of solution in % wt/wt/100

EXAMPLE 7

Preparation of o-nitrobenzylidene, Starting from o-nitrobenzaldehyde

To a round bottom flask was added 510.8 g of isopropanol, 120.9 g of o-nitrobenzaldehyde, 96.8 g of methylacetoacetate, 2.0 g of acetic acid and a calculated volume of methanolic dimethylamine (using the formula below). The mixture was heated to between 39° and 41° C. and kept at this range for 15 minutes and then cooled to between 18° and 22° C. Benzylidine crystals were added as seed, if necessary and granulated for 16 hours. The slurry was cooled to between 0° and 5° C., granulated for one hour. The reaction mixture was filtered, washed with cold isopropanol, and dried overnight in a vacuum oven at 40° C.

moles of dimethylamine×45.09 g (molecular wt. DMA). grams of solution concentration of solution in % wt/wt/100

EXAMPLE 8

Preparation of c-Nifedipine

To a round bottom flask was charged 228 ml of methanol, 37.9 of methylaminocrotonate, and 76.0 g of o-nitrobenzylidene. The reaction mixture was heated to reflux, (67° to 70°) and continued at reflux for 36 hours. The reaction mixture was then cooled to a temperature between 0° and 5° C. and granulated for one hour. The product was filtered and washed first with 95 ml of cold methanol followed by 435 ml of water, and dried in a vacuum oven at 50° to 55° C.

EXAMPLE 9

Recrystallization of Nifedipine

To a round bottom flask was charged 213 ml of ethanol 2B, 50.0 g of crude nifedipine, and 0.4 g of activated charcoal. The mixture was heated to reflux to dissolve the nifedipine and filtered through a hot pressure filter. The filter was washed with 28 ml of hot ethanol 2B. Half the ethanol charged to the pilot was distilled. The mixture was cooled to room temperature and then an ice bath was applied with acetone to cool the mixture to between −10° and −5° C. The reacting mixture was granulated for one hour, filtered, washed with cold Isopropanol, and dried overnight in a vacuum oven at 50° to 55° C.

EXAMPLE 10

The following chart shows the yield of the benzylidene compound when using dimethylamine as the catalyst.

| Catalyst | Starting Material | % isolated yield |
| --- | --- | --- |
| ammonium acetate | o—nb | 30 |
| diethylamine acetate | o—nb | 29 |
| dimethylamine acetate | o—nb | 40 |
| dimethylamine acetate | o—nb | 97 |
| dimethylamine acetate | o—nb | 96 |
| piperidine acetate | acetal | 96 |
| piperidine acetate | acetal | 95 |
| piperidine acetate | acetal | 94 |
| dimethylamine acetate | acetal | 94 |
| dimethylamine acetate | acetal | 96 |
| dimethylamine acetate | acetal | 95 |
| dimethylamine acetate | acetal | 95 |

-continued

| Catalyst | Starting Material | % isolated yield |
|---|---|---|
| dimethylamine acetate | o—nb | 98 |
| dimethylamine acetate | o—nb | 97 |
| dimethylamine acetate | acetal | 95 |

I claim:

1. In the preparation of a 1,4-dihydropyridine of the formula

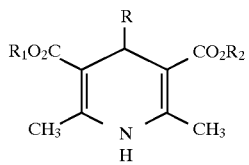

in which

R is a phenyl radical which is optionally substituted once or twice by nitro and/or chlorine, $R_1$ is a $C_1$–$C_4$ alkyl radical which is optionally substituted by a $C_1$–$C_4$ alkoxy group, and $R_2$ is a $C_1$–$C_{12}$ alkyl radical which is optionally substituted by a $C_1$–$C_4$ alkoxy group optionally substituted by an amino group, a trifluoromethyl group or the radical $(C_6H_5CH_2)(CH_3)N$, by preparing an ylidene compound of the formula

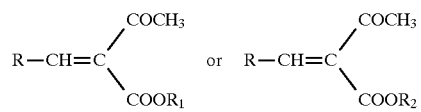

and reacting such ylidene compound with an enamine compound of the formula

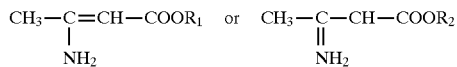

the improvement which comprises preparing the ylidene compound by reaction of a ketocarboxylic ester of the formula

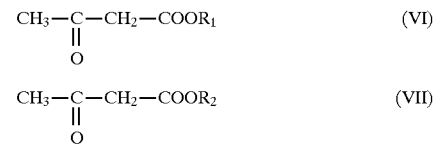

with an aldehyde of the formula RCHO on an acetal of said aldehyde, In an aliphatic alcohol as solvent in the presence of a catalytic amount of dimethylamine acetate at a temperature from about −10° C. up to about 100° C.

2. A process according to claim 1 wherein the reaction is carried out at about 20°–60° C.

3. A process according to claim 1 wherein about 0.01 to 0.07 mole of catalyst is employed per mole of aldehyde compound.

4. A process according to claim 1 wherein about 0.02 to 0.2 mole of catalyst is employed per mole of aldehyde compound.

5. A process according to claim 1 wherein about 0.04 to 0.2 mole of catalyst is employed per mole of aldehyde compound.

6. A process according to claim 1 wherein about 1 to 2 moles of aldehyde are employed per mole of ketocarboxylic ester.

7. A process according to claim 1 wherein about 1 mole of aldehyde is employed per mole of ketocarboxylic ester.

8. A process according to claim 1 In which

R is a 2- or 3nitrophenyl radical, a 2- or 3chlorophenyl radical or a 2,3dichlorophenyl radical, $R_1$ is a methyl, ethyl, propyl, isopropyl, Isobutyl or a propoxyethyl radical, and $R_2$ is a methyl, ethyl, propyl, isopropyl, isobutyl n-decyl, methoxyethyl, methoxyethylamino, propoxyethyl, trifluoromethylmethyl, or the radical $(C_6H_5CH_2)(CH_3)N$.

9. A process according to claim 8, wherein $R_1$ and $R_2$ are the same.

10. A process according to claim 8, wherein $R_1$ and $R_2$ are different.

11. A process according to claim 8, wherein the reaction is carried out at about 20°–60° C., about 0.04 to 0.2 mole of catalyst is employed per mole of aldehyde compound, and about 1 mole of aldehyde is employed per mole of ketocarboxylic ester.

* * * * *